United States Patent
Gagnon et al.

(10) Patent No.: US 6,694,172 B1
(45) Date of Patent: Feb. 17, 2004

(54) FAULT-TOLERANT DETECTOR FOR GAMMA RAY IMAGING

(75) Inventors: Daniel Gagnon, Twinsburg, OH (US); Jerome J. Griesmer, Kirtland, OH (US)

(73) Assignee: Koninklijke Philips Electronics, N.V., Eindhoven (*) Notice: Subject to any disclaimer, the term of this patent is extended or adjusted under 35 U.S.C. 154(b) by 309 days.

(21) Appl. No.: 09/943,912

(22) Filed: Aug. 31, 2001

Related U.S. Application Data
(60) Provisional application No. 60/300,357, filed on Jun. 23, 2001.

(51) Int. Cl.[7] ................................................. A61B 6/00
(52) U.S. Cl. ............. 600/436; 250/370.09; 250/370.01; 250/363.07; 250/363.02
(58) Field of Search ................................. 600/407, 431, 600/436, 427; 250/370.08, 370.01, 370.13, 303, 371, 362, 363.07, 363.08, 363.09, 363.1, 363.02, 369, 308, 363.04; 604/27–28; 378/207, 901, 62–63, 4

(56) References Cited

U.S. PATENT DOCUMENTS

| | | | |
|---|---|---|---|
| 4,074,778 A | 2/1978 | Morrell et al. ............... 175/91 |
| 4,090,080 A | 5/1978 | Tosswill ..................... 250/366 |
| 4,223,221 A | * 9/1980 | Gambini et al. ......... 250/363.07 |
| 4,262,207 A | 4/1981 | Tosswill ..................... 250/505 |
| 4,982,096 A | 1/1991 | Fujii et al. .................. 250/367 |
| 5,077,770 A | 12/1991 | Sammon ..................... 378/101 |
| 5,152,592 A | 10/1992 | Krayer ........................ 312/238 |
| 5,296,709 A | * 3/1994 | Jarkewicz ............... 250/363.07 |
| 5,530,249 A | 6/1996 | Luke ........................... 250/374 |
| 5,645,190 A | 7/1997 | Goldberg ..................... 220/674 |
| 5,663,566 A | * 9/1997 | Maniawski et al. ......... 250/369 |
| 5,967,983 A | 10/1999 | Ashburn ...................... 600/436 |
| 5,969,360 A | 10/1999 | Lee |
| 5,991,357 A | 11/1999 | Marcovici et al. ............. 378/19 |
| 6,046,454 A | 4/2000 | Lingren et al. ......... 250/370.01 |
| 6,055,450 A | 4/2000 | Ashburn ...................... 600/431 |
| 6,091,070 A | 7/2000 | Lingren et al. ......... 250/370.09 |

OTHER PUBLICATIONS

Zeng et al., "Eigen Analysis of Cone–Beam Scanning Geometries," in *Three–Dimensional Image Reconstruction in Radiation and Nuclear Medicine* (Grangeat et al., Eds.), Kluwer Academic Publishers, Netherlands, pp. 75–86(1996).

Zeng et al., "A Cone Beam Tomography Algorithm for Orthogonal Circle–and–Line Orbit," *Phys. Med. Biol.*, vol. 37, No. 3, pp. 563–577 (1992).

(List continued on next page.)

Primary Examiner—Eleni Mantis Mercader
(74) Attorney, Agent, or Firm—Fay, Sharpe, Fagan, Minnich & McKee, LLP

(57) ABSTRACT

A nuclear imaging apparatus includes a radiation detector comprising an array (18) of solid state detector elements (22) responsive to incident gamma radiation by emitting a current spike. A pixel correction processor (44) detects defective detector elements in the array and a flood correction circuit (66) corrects detected radiation events (70) based on sensitivity differences between a plurality of groupings of detector elements in the array. A reconstruction processor (76) reconstructs an image representation from the corrected radiation events (74).

18 Claims, 6 Drawing Sheets

OTHER PUBLICATIONS

Webb et al., "Monte Carlo Modelling of the Performance of a Rotating Slit–Collimator for Improved Planar Gamma–Camera Imaging," *Phys. Med. Biol.,* vol. 37, No. 5, pp. 1095–1108 (1992).

Mauderli et al., "A Computerized Rotating Laminar Radionuclide Camera," *J. Nucl. Med,* vol. 20, pp. 341–344 (1979).

Entine et al., "Cadmium Telluride Gamma Camera," *IEEE Transactions on Nuclear Science,* vol. NS–26, No. 1, pp. 552–558 (1979).

Urie et al., "Rotating Laminar Emission Camera with GE–Detector: Experimental Results," *Med. Phys.,* vol. 8, No. 6, pp. 865–870 (1981).

Mauderli et al., "Rotating Laminar Emission Camera with GE–Detector: An Analysis," *Med. Phys.,* vol. 8, No. 6, pp. 871–876 (1981).

Malm et al., "A Germanium Laminar Emission Camera," *IEEE Transactions on Nuclear Science*, vol. NS–29, No. 1, pp. 465–468 (1982).

Mauderli et al., "Rotating Laminar Emission Camera with GE–Detector: Further Developments," *Med. Phys.,* vol. 14, No. 6, pp. 1027–1031 (1987).

\* cited by examiner

FAULT-TOLERANT DETECTOR FOR GAMMA RAY IMAGING

CROSS-REFERENCE TO RELATED APPLICATIONS

The present application claims the priority benefit under 35 U.S.C. §119(e) of the U.S. Provisional Application Serial No. 60/300,357, filed Jun. 23, 2001. The Provisional Application is incorporated herein by reference in its entirety.

INCORPORATION BY REFERENCE

The present application incorporates herein by reference thereto the following applications and U.S. Patents in their entireties: U.S. Application of Gagnon et al., Ser. No. 09/206,508, filed Dec. 7, 1998, now U.S. Pat. No. 6,359,279 entitled DETECTOR FOR NUCLEAR IMAGING; U.S. Application of Zeng, Ser. No. 09/708,960, filed Nov. 8, 2000, now U.S. Pat. No. 6,603,123 entitled CORRECTION FOR DEPTH-DEPENDENT SENSITIVITY IN ROTATING SLAT-HOLE GAMMA CAMERA; U.S. Application of Griesmer et al., Ser. No. 09/721,817, filed Nov. 24, 2000, now U.S. Pat. No. 6,586,744 entitled METHOD OF COOLING HIGH DENSITY ELECTRONICS; U.S. Application of Griesmer et al., Ser. No. 09/722,124, filed Nov. 24, 2000, now U.S. Pat. No. 6,472,668 entitled HIGH VOLTAGE DISTRIBUTION SYSTEM FOR CZT ARRAYS; U.S. Application of Kline et al., Ser. No. 09/722,131, filed Nov. 24, 2000, now U.S. Pat. No. 6,459,086 entitled DIGITAL PEAK DETECTOR FOR RADIATION DETECTION SYSTEM; U.S. Application of Kline et al., Ser. No. 09/722,132, filed Nov. 24, 2000, now U.S. Pat. No. 6,472,667 entitled DATA REDUCTION ARCHITECTURE FOR NUCLEAR MEDICINE IMAGER; U.S. Application of Natterer et al., Ser. No. 09/808,931, filed Mar. 15, 2001, now U.S. Publication No. 20020177773 entitled FAST TRANSFORM FOR RECONSTRUCTION OF ROTATING SLAT-HOLE DATA; U.S. Application of Zeng et al., Ser. No. 09/809,467, filed Mar. 15, 2001, now U.S. Pat. No. 6,593,576 entitled VARIABLE ANGULAR SAMPLING RATE FOR ROTATING SLAT-HOLE FOR GAMMA CAMERAS; U.S. Application of Zeng et al., Ser. No. 09/808,935, filed Mar. 15, 2001, entitled FOCUSED ROTATING SLAT-HOLE FOR GAMMA CAMERAS. Each of the above-incorporated applications is assigned or subject to assignment to the assignee of the present application.

BACKGROUND OF THE INVENTION

The present invention relates to the art of nuclear medical imaging. It finds particular application in conjunction with rotating one-dimensional (1D) slat-collimated gamma cameras and single photon emission computed tomography (SPECT), and will be described with particular reference thereto. However, it is to be appreciated that the present invention is also amenable to other like applications and other diagnostic imaging modes, such as positron emission tomography (PET).

Nuclear imaging employs a source of radioactivity to image the anatomy of a subject. Typically, a radiopharmaceutical is injected into the patient. Radiopharmaceutical compounds contain a radioisotope that undergoes gamma-ray decay at a predictable rate and characteristic energy. Various scanning techniques exist in which the emitted γ-rays are detected. Based on information such as detected position and energy, the radiopharmaceutical distribution is located in the body and a representation of some feature of the subject, such as an organ, abnormality, etc., is reconstructed.

In a traditional Anger-type camera, the detector includes a scintillation crystal that is viewed by an array of photomultiplier tubes. The heads have collimators disposed between the crystal and the subject to limit the trajectory along which radiation can be received. Typically, the collimators are thick lead plates with an array of apertures or bores. Radiation traveling in a trajectory through one of the bores strikes the crystal; whereas radiation traveling in other trajectories hits the collimator and is absorbed. In this manner, each scintillation defines a ray, typically perpendicular to the face of the crystal, although magnifying and minifying collimators are also known. The thicker the collimator, the more accurately the ray trajectory is defined, but count efficiency or sensitivity is reduced since more radiation is absorbed in the collimator without reaching the detector.

Rather than using a single, large scintillator and photomultiplier tubes, others have proposed using an array of small scintillators, each associated with a photodiode or other photosensitive device which senses a scintillation in each individual scintillation crystal. Other types of individual solid-state detectors have also been suggested.

To improve the amount of radiation that reaches the detector, it has been proposed to use collimator sheets in a single direction across a row of detectors such that detected radiation defines a plane instead of a ray. The detectors are rotated to collect the planes at many angles. For three-dimensional images, the detector was positioned at a plurality of locations around the subject and the rotating data collection process repeated.

Solid state radiation detectors, such as cadmium-zinc-telluride (CZT) detectors, cadmium-telluride detectors, and the like, are also known, which utilize the photoelectric effect to detect radiation. That is, received radiation photons liberate electrons from their orbits around atoms of the target material. A high bias voltage is applied across the detector material to aid the photoelectric phenomenon and electron propagation. The electrons are detected as an electrical signal. Although very good performance can generally be expected from room-temperature CZT, sometimes a pixel is defective, for example, due to crystal impurities, crystal boundaries, electrical contacts, and other reasons.

In a conventional two-dimensional array, a dead pixel can hardly be tolerated and, techniques are known to avoid "holes" in the image, such as substituting the value of an adjacent pixel, substituting an "average" value of pixels neighboring the dead pixel, etc. However, such techniques degrade spatial resolution and sensitivity. In the case of pixels having poor energy resolution, their presence, too, degrades performance of the two-dimensional array, although an ill-behaved pixel is generally more tolerable than no pixel at all.

The process of selecting and testing CZT crystals for two-dimensional arrays adds a significant cost to an already expensive technology and might, in practice, lead to a substantial relaxation of the performance criteria.

The present invention provides a new and improved method and apparatus that overcome the above referenced problems and others.

SUMMARY OF THE INVENTION

In accordance with one aspect of the present invention, a nuclear imaging apparatus comprises a radiation detector including a plurality of rows of detector elements, which generate an output pulse in response to each detected radiation event. A rotor rotates the radiation detector and a plurality of summing circuits, each connected with one of the detector element rows, generate a sum of the output pulses therefrom during a sampling period. A correction circuit adjusts the sums with correction factors, each row having a preselected correction factors. A reconstruction processor reconstructs an image representation from the adjusted sums and rotational position of the detector information corresponding to each sampling period.

In accordance with another aspect of the present invention, a nuclear imaging apparatus includes a radiation detector comprising an array of solid state detector elements responsive to incident gamma radiation by emitting a current spike. A pixel correction processor detects defective detector elements in the array and a flood correction circuit corrects detected radiation events based on sensitivity differences between a plurality of groupings of detector elements in the array. A reconstruction processor reconstructs an image representation from the corrected radiation events.

In a further aspect, a method of diagnostic imaging includes exposing a solid state radiation detector to a known radiation source. The radiation detector comprises a two-dimensional array of detector elements or pixels generating a detectable signal responsive to incident gamma radiation, and each detector element comprising a distinct channel. Radiation events are detected at each detector element and defective and nondefective pixels are identified and detector element correction values are calculated to normalize the energy spectrum of each nondefective pixel. An energy window is defined based on the normalized spectra to distinguish those photons having the energy characteristic of the radiation source. Also, a weighting factor for each row of pixels is calculated to scaling each row to a nominal value when the detector is exposed to a known radiation source. A radioactive isotope is injected into a subject located in an imaging region and the detector array is rotated while detecting radiation events indicative of nuclear decay. Multiple planar projections are generated of an examination region at a plurality of angular orientations, wherein radiation events from the defective pixels is either not recorded or discarded. The detector array is moved around a longitudinal axis of the subject and the steps of rotating and detecting are repeated. The detected radiation events are collected by row and corrected with the weighting factors to generate corrected data. An image representation of the subject is reconstructed using the corrected data.

In yet another aspect, a method of calibrating a nuclear imaging device includes exposing a solid state radiation detector to a known radiation source. The radiation detector comprises a two-dimensional array of detector elements or pixels generating a detectable signal responsive to incident gamma radiation, and each detector element comprising a distinct channel. Radiation events are detected at each detector element and defective and nondefective pixels are identified and detector element correction values are calculated to normalize the energy spectrum of each nondefective pixel. An energy window is defined based on the normalized spectra to distinguish those photons having the energy characteristic of the radiation source. Also, a weighting factor for each row of pixels is calculated to scaling each row to a nominal value when the detector is exposed to a known radiation source.

Another advantage of the present invention is that a gamma camera with improved performance is provided, especially in terms of energy resolution.

Another advantage is that the cost of the array is substantially decreased by allowing the use of detector crystals that would ordinarily be rejected due to the presence of one or more bad pixels.

Another advantage of the present invention is that dead and defective pixels can be turned off to improve energy resolution without any loss of spatial resolution and only a minimal effect on sensitivity.

Still further benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENT

Figure 1:
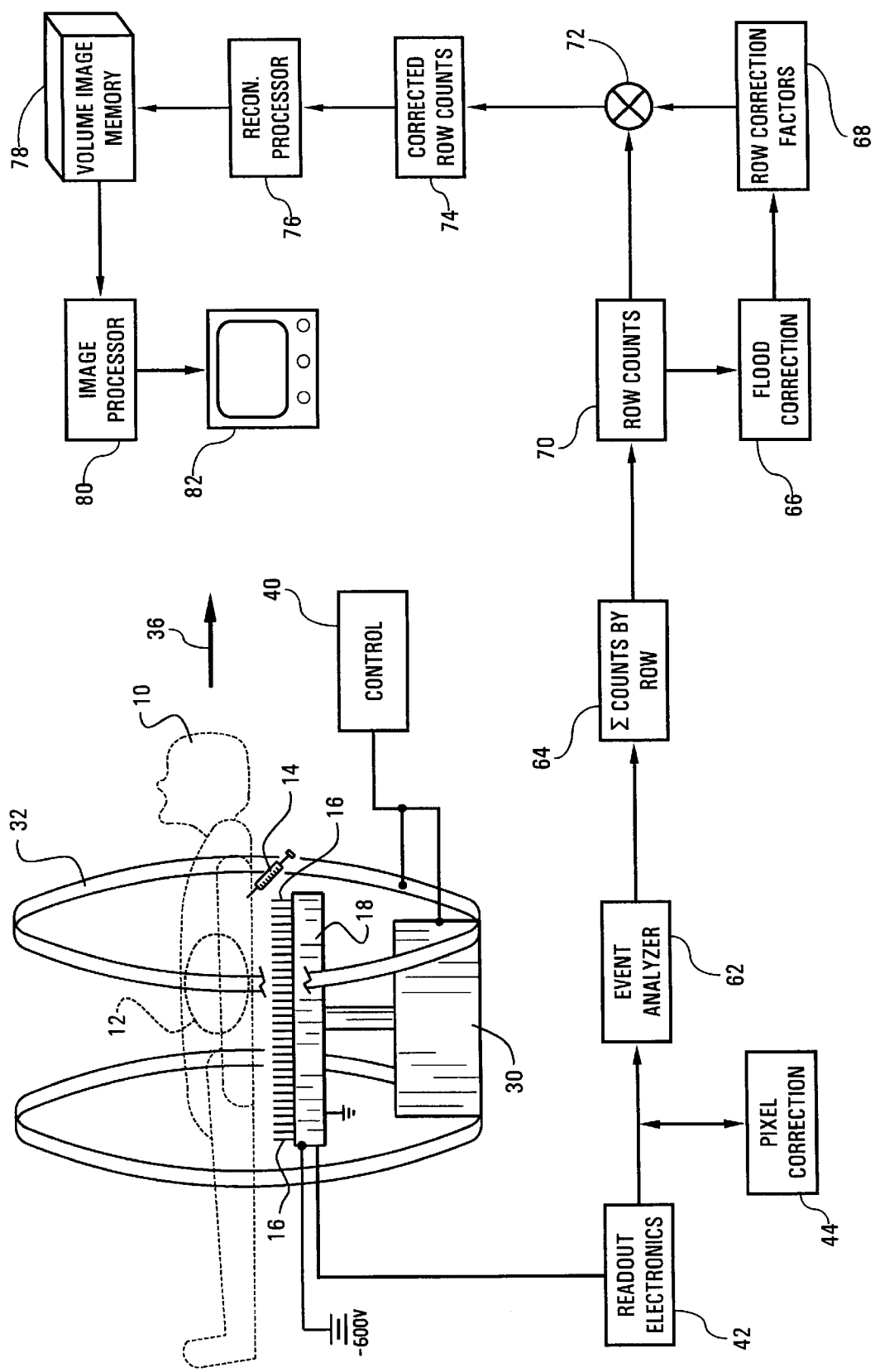
FIG. 1 is a diagrammatic illustration of a nuclear imaging device in accordance with the present invention.
Figure 2:
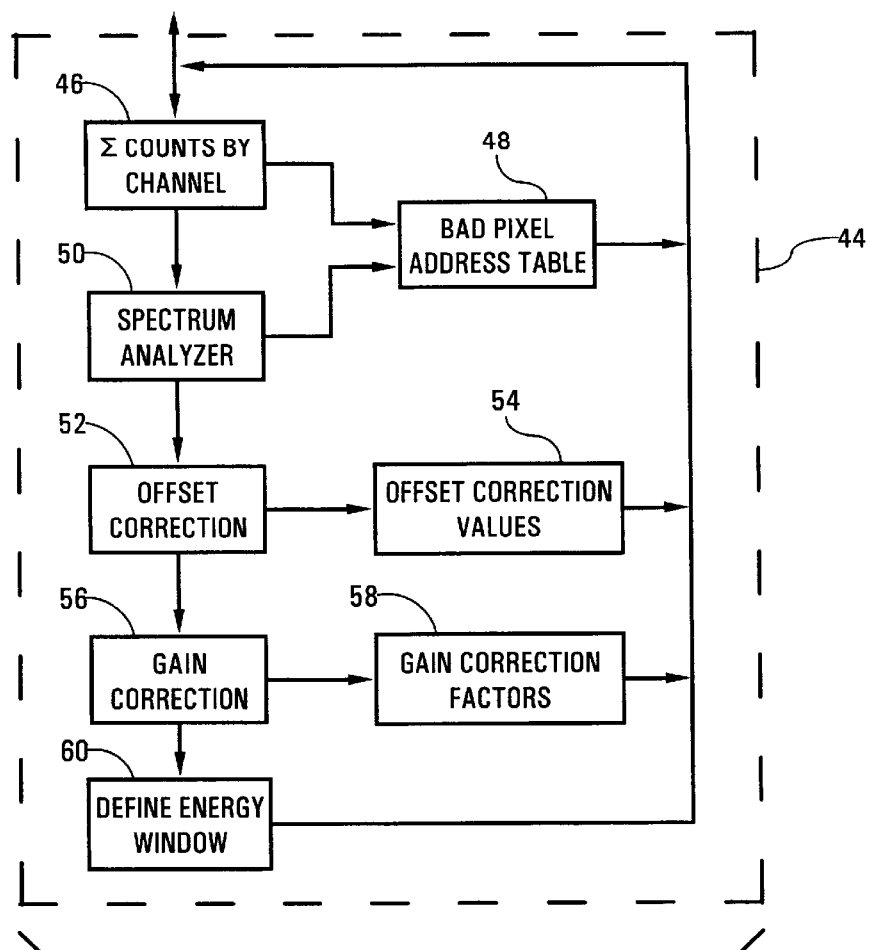
FIG. 2 is a block diagram illustrating the pixel correction processor in greater detail.
Figure 3:
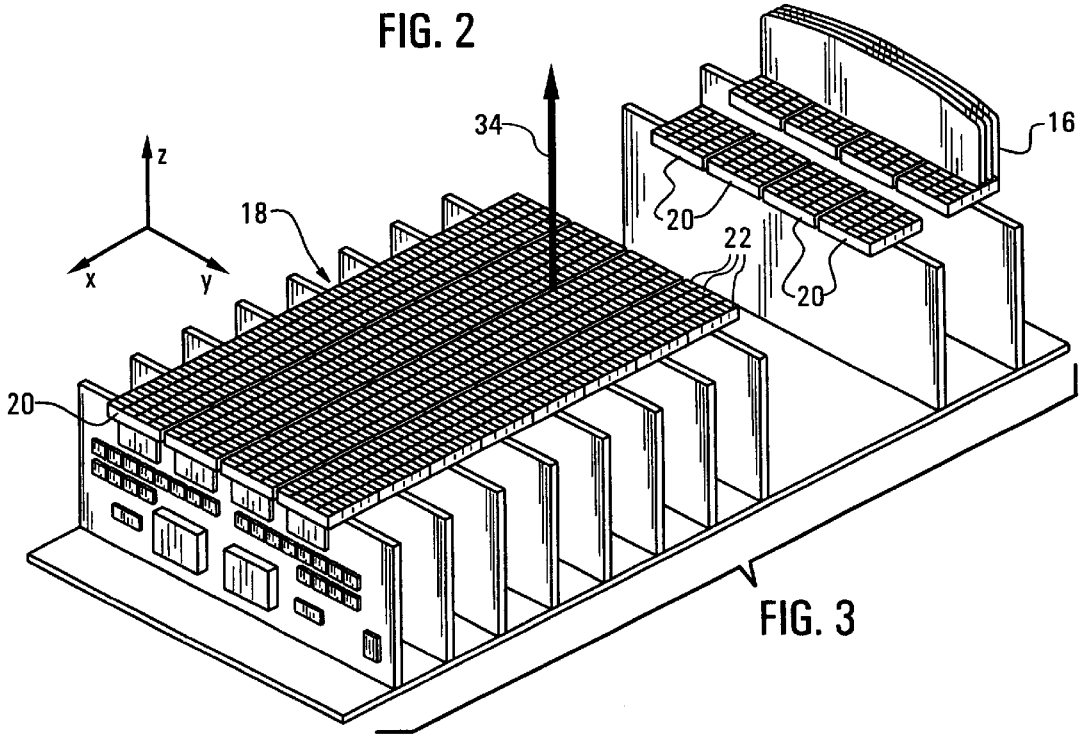
FIG. 3 is a perspective view of a detector array and collimator arrangement in accordance with the present invention.

With reference to FIGS. 1–3, a region of interest 12 of a subject 10 is disposed in an imaging region. In the preferred embodiment, a radiopharmaceutical 14 is injected into the subject, near the region to be imaged. For example, if a physician wanted to view a blockage in an artery, the isotope would be injected into the bloodstream upstream from the blockage. As another example, the radiopharmaceutical 14 is injected into the circulatory system and its selective absorption by tissue of interest is monitored.

Atomic nuclei of the radioactive isotope decay over time. Energy is released at the time of decay in the form of a radiation photon, more specifically, a γ-ray of characteristic energy.

Many of the γ-rays produced during an imaging process are lost, propagating in useless directions. However, some of the γ-rays pass through collimators 16, thin tungsten, lead, or other high-z vanes or septa in the preferred embodiment, and strike a detector array 18. In the preferred embodiment, the detector array 18 includes a linear array of solid state detector elements, such as cadmium telluride crystals, cadmium zinc telluride (CZT) crystals, or other semiconductor detectors. When a γ-ray strikes the detector, it frees many electrons from their bonds to the detector material. These electrons are propelled by an applied bias voltage across the thickness of the crystal and form an electrical signal.

In a preferred embodiment, the linear detector array is defined by multiple two-dimensional detector arrays or tiles 20. The collimators 16 extend in the y-direction. For imaging purposes, the detector array 18 is treated as a one-dimensional array in the direction transverse to the collimator vanes, i.e., the x-direction. That is, for acquiring image data, the detectors 22 of a single row are all sampled together as if they were a single elongated crystal for higher photon counts. As such, each row between the collimator vanes defines a plane of activity and the reconstruction is performed using plane integral reconstruction techniques as are known to persons skilled in the art.

The detector array 18 is mounted on a head 30 that is mounted to a gantry 32, which is indexed around the region of interest. In one embodiment, a motor spins the detector array about a center axis 34 passing through the center of the array 18 and extending in the z-direction. In alternative embodiments, the detector array is rotated about an axis offset from the center point of the detector array radiation receiving surface. In still further embodiments, more complex spin orbits, such as a Reuleaux orbit, are used. More complex rotational movements about a longitudinal axis of the subject are also contemplated.

While spinning, the detectors move through parallel to a longitudinal axis 36 of the subject 10, and 90° from the longitudinal axis 36. A motor control 40 selects a range of motion of the detector array 18, if any, within the rotatable gantry and the rotation of the gantry 32. These two motions of the detector array 18, that is, the spin orbit about its own axis, and rotation of the head 30 about a long axis of the subject 10, give the detector array 18 a sufficient variety of views of the subject 10 to reconstruct an accurate three-dimensional image representation.

During detection of radiation events, the spin motion of the detector array can be continuous or performed in stepwise (step and shoot) fashion, or any combination thereof. Any translation of the detector head 30, e.g., rotation of the head about a long axis of the subject and/or translation of the head parallel to a long axis of the subject can likewise be performed in continuous or stepwise fashion, or any combination thereof.

In one embodiment, the detector array 18 spins about its own center, while the head 30 remains stationary. With parallel collimators perpendicular to the array 18, the array 18 spins 180°. It is to be understood that this value is a minimum range of rotation, enough to obtain a full set of views. The array 18 could also perform more spin rotations to increase photon counts in that position and integrate the counts over a longer duration. For parallel collimators 16 oriented in a manner other than perpendicular to the array 18, 360° of spin rotation is performed to obtain a full view.

Various other spin and rotational trajectories are also contemplated. Also, the detector array can be stationarily mounted to the movable gantry, which is indexed around to region of interest. It is also not necessary that the detectors be moved or rotated with respect to the patient; relative motion may be provided by moving the patient with respect to the detectors.

Exemplary slat-hole scanners of the type for use in conjunction with the present invention may have characteristics as described in the incorporated copending U.S. applications referenced above.

In operation, the array is first calibrated on a pixel-by-pixel basis, and is again calibrated on a row-by-row basis for row uniformity or sensitivity correction. For pixel correction, the array 18 is exposed to a known radioactive flood source emitting at the desired energy level.

In the pixel calibration mode, the response of each pixel is individually recorded and examined. The radiation events are acquired by readout electronics 42, which includes analog-to-digital converters, multiplexers, and so forth, as necessary so that each pixel is treated as a separate channel. The events within a wide energy window (e.g., 200% of the photopeak) are detected and analyzed by pixel correction circuit or processor 44, the functional components of which are illustrated in FIG. 2.

The pixel correction processor 44 includes a counter 46, which sums the number of radiation events for each channel. A sufficient number of counts is to provide an accurate or reproducible depiction of each pixels energy spectrum. In an exemplary embodiment, the detector array is made up of tiles having 4×8 pixels each in the y- and x-directions, respectively. The array consists of tiled rows of 4 of the chips extending end-to-end in the y-direction, thus forming a 128-pixel array arranged in 8 rows of 16 pixels each. The array is extended in the x-direction with additional tiles in like manner, and a collimator is placed between each of the rows. In a preferred embodiment, a tiled array consists of 4 chips by 24 chips to provide a 16×192 pixel array, i.e., 192 rows of 16 pixels each. In this exemplary embodiment, which has about 3,072 pixels, about 33,000,000 counts are used for pixel correction, corresponding to about 11,000 counts per pixel.

In determining which pixels are "dead," the number of counts recorded by each pixel is counted. If the number of recorded radiation events does not reach some preselected threshold value, that pixel is considered to be defective or "dead." The threshold can be, for example, some percentage of the expected number of counts, i.e., in the range of from about 10–50% of the expected number of counts. In the described example in which 11,000 counts are expected per pixel, a preferred screening threshold, below which a pixel is considered to be dead, is about 2,000 recorded events. The addresses of those pixels that fail to reach the threshold number of counts are logged or stored in a memory 48, and the dead pixels are turned off. This can be done by a number of methods. In the preferred embodiment, the bad pixels are eliminated by storing a gain correction factor of zero, e.g., in the gain correction table 58. Other methods of eliminating the bad pixels are also contemplated. For example, the pixel can be turned off electronically, e.g., by disabling or disconnecting the bad pixels from the front end electronics. Also, the identified bad pixels can be eliminated by disregarding these pixels' contributions at any later stage during data acquisition and processing, e.g., when culminating events in an image.

Figure 5:
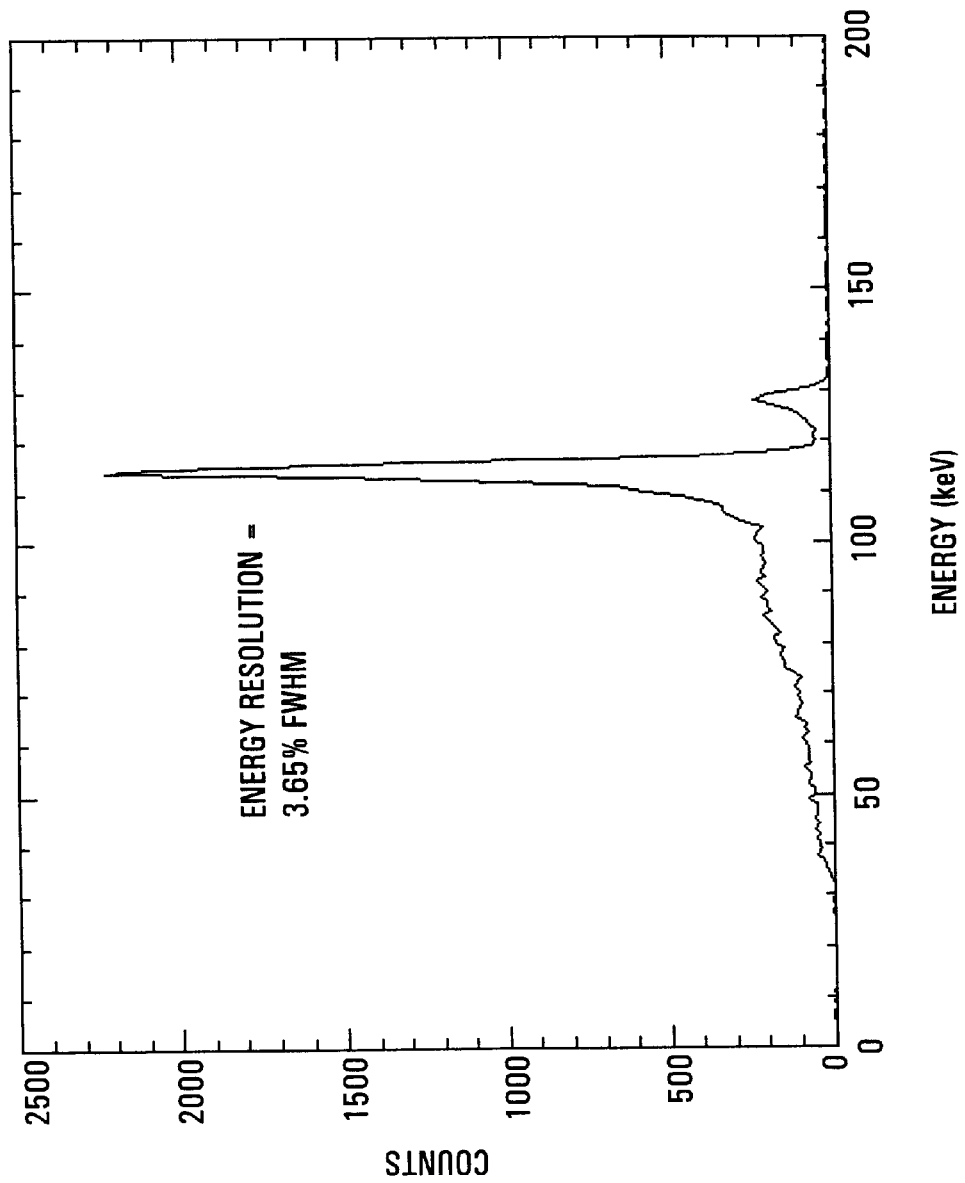
FIG. 5 is an energy spectrum of a CZT detector element or pixel, which exhibits good energy resolution.
Figure 6:
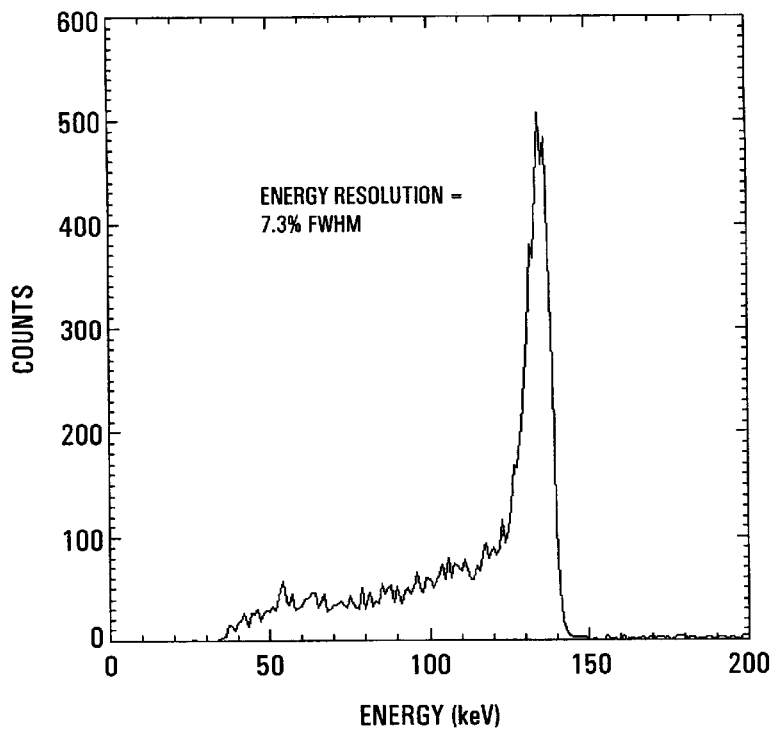
FIGS. 6–9 are energy spectra of CZT pixels exhibiting poor energy resolution and which are typical of pixel energy responses of pixels which are turned off in accordance with the subject invention.
Figure 7:
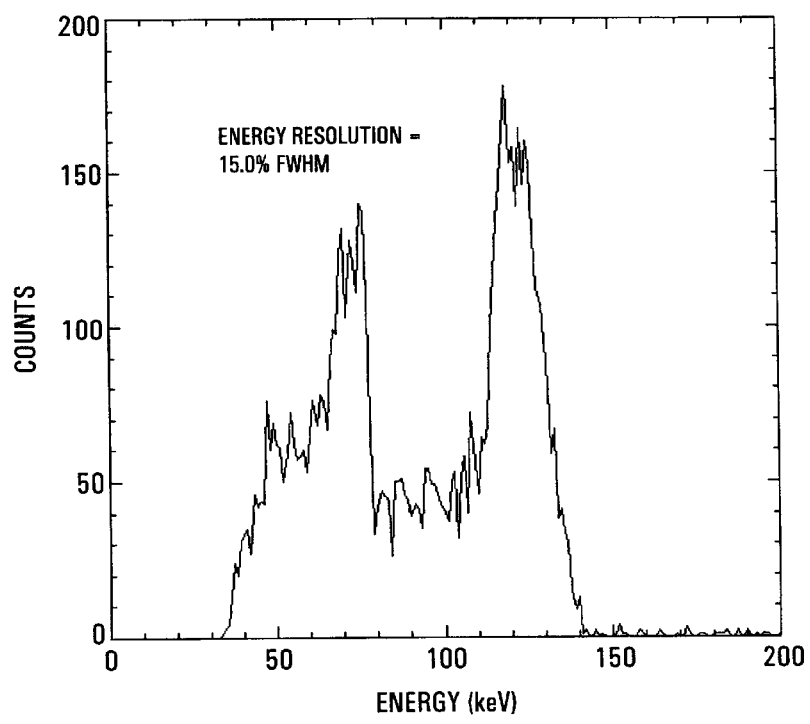
Figure 8:
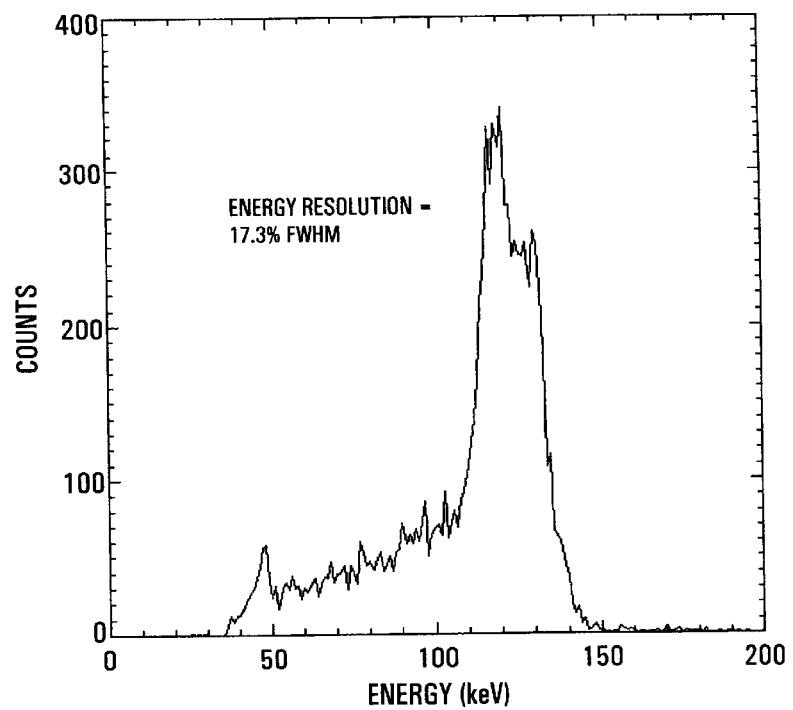
Figure 9:
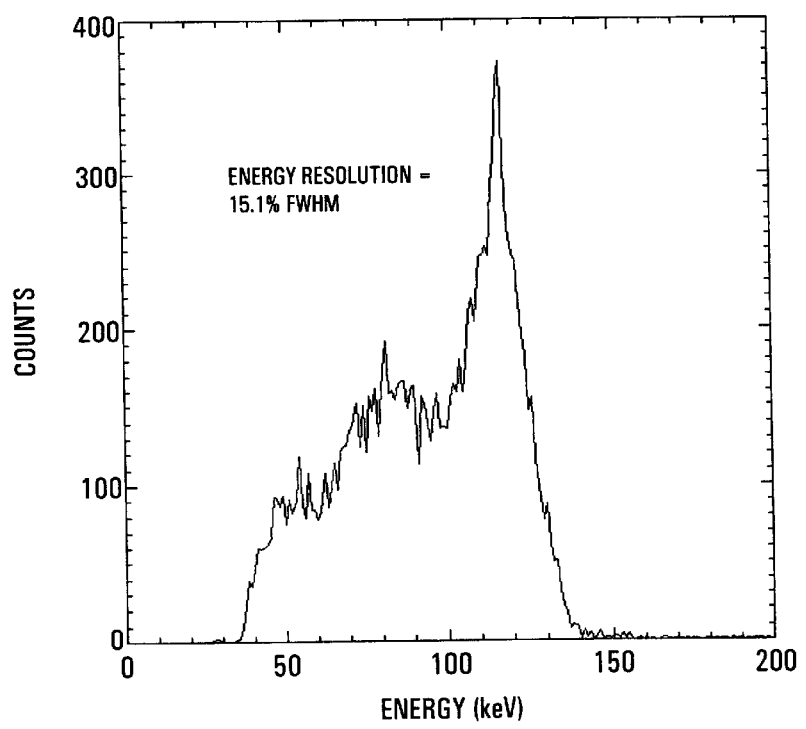

For each pixel that records at least the threshold number of counts, the counts are sorted according to pixel and energy, e.g., using a multichannel analyzer and a pulse height analyzer, to generate a spectrum. The spectra are examined by a spectrum analyzing circuit 50 for a prespecified degree of energy resolution. The majority of pixels will exhibit good energy resolution, as illustrated in FIG. 5. Some pixels, however, do not exhibit a single or well-defined peak and these pixels, exhibiting poor energy resolution ability, are also turned off or discarded in accordance with the present invention. Exemplary spectra of pixels having poor energy resolution and which would be discarded in accordance with the present invention are shown in FIGS. 6–9. The pixel addresses corresponding to pixels lacking the selected energy resolution are likewise logged in the table or database 48 and disabled as described above.

Since the dead and poor energy pixels (herein referred to collectively as "bad" or "defective" pixels) are not used, they are not subject to any further correction. The good pixels are normalized using a pixel-by-pixel correction scheme. A baseline offset correction value is determined for each pixel when no events are occurring by an offset correction circuit 52 and pixel specific values are stored in a look-up table or other storage device 54. Also, a gain correction factor is also calculated for each pixel using a gain correction circuit 56 and pixel specific gain correction factors are stored in a look-up table or other storage device 58. In operation, the corresponding offset correction value from table 54 is subtracted from the channel output signal and the resultant difference is multiplied by the pixel-appropriate gain correction factor from the table 58.

After the spectra are normalized, an energy window is defined. An energy window is defined based on the normalized spectra to discriminate photons having the energy characteristic of the radiation source, e.g., to eliminate scatter or noise, and so forth. Preferably, the window is defined in accordance with a prespecified energy criteria relative to the photopeak. In an especially preferred embodiment, the energy window is defined by specifying a energy width of from about 10–15% of the photopeak energy, approximately centered about the photopeak, most preferably about 10%.

Preferably, the pixel correction calibration is performed for multiple radioactive sources, and multiple pixel correction values and energy window definitions are stored, i.e., for each radioactive source to be used for imaging. The appropriate values are then recalled in later studies as appropriate for the radioactive source used. Alternatively, due to the linearity of the solid state system, one calibration can be used for a range of energy windows. The present invention is particularly well-suited for studies in which plural radioactive tracers and plural energy windows are used. The energy resolution that is achievable with the present invention makes it possible to use radionuclides together having energies which cannot be discriminated by conventional nuclear cameras.

After the pixel correction calibration is complete, a flood calibration acquisition for row sensitivity or uniformity is performed. This row-by-row calibration is performed after the pixel correction. That is, the defective pixels are turned off or their contributions otherwise disregarded, the pixel outputs are normalized using the offset and gain correction factors, and the radiation events are screened using the defined energy window.

The detector array 18 is exposed to a statistically significant number of photons from the radioactive flood source, the number of photons being a sufficient number to ensure consistency from one calibration to the next. Preferably, the number of photons is that which provides a variation of ±1% or better. For example, in the above described exemplary embodiment having about 3,072 pixels, the number of photons in the row uniformity calibration acquisition is about 23,000,000, that is, about 7,500 photons per pixel corresponding to about 120,000 photons per 16-segment row.

During the row-sensitivity calibration acquisition, pixel events are read out by the electronics 42 and corrected by the pixel correction processor 44, i.e., using the stored offset and gain correction values. An event analyzer 62 detects radiation events falling within the defined energy window and a counter 64 sums the valid photon events by row. The row counts are stored in a buffer, archive, or other memory 70.

A flood correction circuit 66 compares the number with a nominal number of counts per row, i.e., the number of counts expected based on the number of photons used in the calibration, and calculates a weighting factor for each row. The weighting factors scale each row to the nominal, and are stored in a memory 68. For example, if the number of counts in a row has 10% fewer counts than the nominal, a weighting factor to increase the number of counts for that row by 10% is used. Conversely, a greater than the nominal number of counts might be recorded for a row, such as a row having no defective pixels and/or one or more extra-sensitive pixels. Thus, a scaling factor for each row, which reduces the number of counts to nominal, is stored in the memory 68. In this manner, the uniformity correction compensates for the eliminated defective pixels, in addition to nonuniformity caused by sensitivity differences between the good pixels.

In a preferred embodiment, the number of counts from each row is further examined to ensure that it is within some preselected deviation of the nominal number of counts. A preferred maximum row sensitivity deviation is about 12% of the nominal number of counts, although values other than 12% of the nominal can be used, the image quality improving or deteriorating with count deviations which are lesser or greater, respectively. Advantageously, because the array is made up of 4×8 pixel tiles which can be rearranged, the tiles are rearranged to more uniformly distribute the dead pixels among the rows when a row having a sensitivity outside the permitted range is encountered. For example, if a particular row has so many dead pixels that it decreases the count sensitivity to a point beyond the preselected sensitivity deviation range (e.g., 12% of nominal), the tiles can be repositioned within the array to reduce the number of dead pixels in that row. The rearrangement can be performed by a number of methods. For example, a rearrangement to more uniformly distribute the eliminated pixels throughout the rows can be determined based on the locations of the bad pixels, e.g., using a computer process to effect the redistribution, or, through a manual inspection of the bad pixel locations. In a further embodiment, the flood calibration events are sorted according to pixel, and a pixel tile rearrangement that optimizes the sensitivity uniformity among the various rows is computed.

Although the present invention is described in reference to the preferred embodiment in which separate pixel-correction and row-sensitivity acquisitions are performed, in alternative embodiment, only a single flood acquisition is performed to generate the pixel correction factors and to define the energy window as described above. The row-sensitivity correction factors are then determined by reanalyzing the pixel correction data. The data is corrected to normalize the pixels and the data is screened using the defined energy window.

Figure 4:
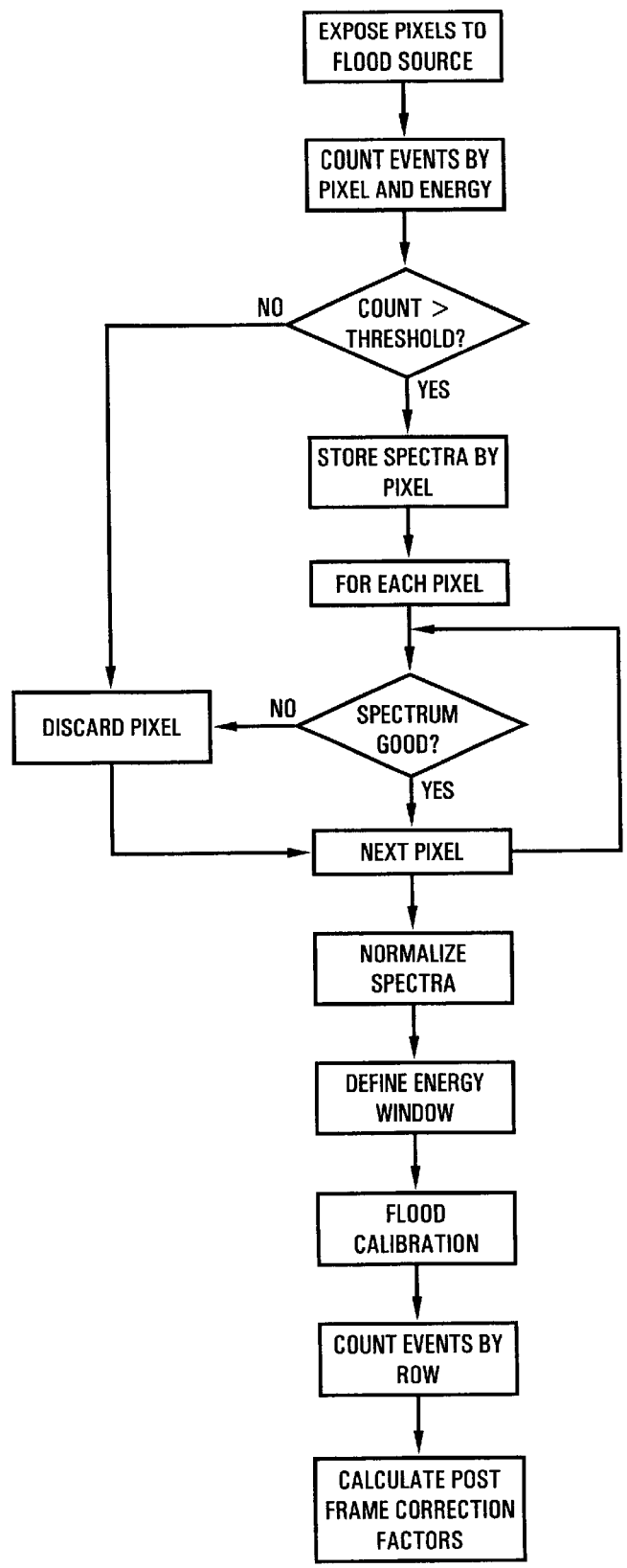
FIG. 4 a flow diagram illustrating an exemplary method of the present invention.

After the pixel correction factors, energy window definition, and the row sensitivity correction factors are determined, they are stored for later use when imaging a subject. A flow chart summarizing the above-described calibration technique is shown in FIG. 4.

In an imaging mode of operation, the subject 10 to be imaged is injected with the radionuclide and multiple plane integral views from around the subject 10 are acquired to reconstruct a three-dimensional view of the imaging region 12. The pixel signals are acquired by the readout electronics 42 and corrected for offset and gain by pixel correction function 44. The event analyzer 62 detects valid events, i.e., events within the defined energy window. The event analyzer also sorts the events by energy in a dual- or multiple-energy study. The processor 64 sorts the valid radiation events by row and the collected row data are stored in a memory 70. As the rotatable gantry 32 is rotated to different angular positions around the subject, a plurality of projection images from different angular orientations are collected. A multiplication function 72 multiplies the row counts by the row correction factors 68, and the resultant products are stored in a memory 74 as corrected row counts. A reconstruction processor 76 backprojects or otherwise reconstructs the corrected data from the memory 74 into a volumetric image representation for storage in a volumetric image memory 78. An image processor 80 under operator control withdraws selected portions of the volumetric image representation and converts them into appropriate form for display on a video monitor or other human-readable display device 82.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A nuclear imaging apparatus comprising:
   a radiation detector including a plurality of rows of tiles of detector elements, each of the detector elements generating an output pulse in response to each detected radiation event;
   a rotor which rotates the radiation detector;
   an analyzer which compares the response of each detector element with preselected response criteria when the radiation detector is subjected to a calibration radiation source;
   read out electronics which suppresses output pulses from detector elements whose response fails to meet the preselected response criteria;
   a plurality of summing circuits, each summing circuit being connected with one of the plurality of rows of tiles of detector elements to generate a sum of the output pulses therefrom during a sampling period;
   a correction circuit which adjusts the sums with correction factors, each row having a preselected one of the correction factors after the output pulses from detector elements whose response fails to meet the preselected response criteria are suppressed; and
   a reconstruction processor that reconstructs an image representation from the adjusted sums and rotational position of the radiation detector corresponding to each sampling period.

2. The apparatus of claim 1, wherein said correction circuit receives the sums while the detector elements are subjected to a the calibration radiation source, determines a deviation between the sum of each row and a nominal sum, and calculates a corresponding correction factors to correct each sum to the nominal sum.

3. A nuclear imaging apparatus comprising:
   a radiation detector comprising an array of solid state detector elements arranged in a plurality of rows of tiles of detector elements, the detectors elements responsive to incident gamma radiation by emitting output pulses;
   a pixel correction processor which detects defective detector elements in the array;
   means for comparing a spectral response of each detector element with preselected spectral response criteria when the radiation detector is subjected to a calibration radiation source;
   read out electronics which suppresses output pulses from defective detector elements whose spectral response fails to meet the preselected response criteria;
   a plurality of summing circuits, each summing circuit being connected with one of the plurality of rows of tiles of detector elements to generate a sum of the output pulses therefrom during a sampling period;
   a flood correction circuit which corrects detected radiation events based on sensitivity by adjusting the sums with correction factors, each row having a preselected one of the correction factors after the output pulses from defective detector elements are suppressed; and
   a reconstruction processor which reconstructs an image representation from the corrected radiation events.

4. The apparatus of claim 3, wherein the flood correction circuit compares the detected radiation events for each row with a nominal number of counts and calculates a corrective weighting factors, one for each row, the corrective weighting factors calculated to scale each row to the nominal number.

5. The apparatus of claim 3, the pixel correction processor including:
   a pulse height analyzer for generating an energy spectrum for each pixel;
   an a pixel offset correction circuit for normalizing the detector elements with respect to a baseline voltage when no gamma radiation is incident on the radiation detector; and
   a gain correction circuit for normalizing the detector elements with respect to pulse height of the current spikes when gamma radiation is incident on the radiation detector.

6. The apparatus of claim 3, wherein:
   the pixel correction processor utilizes gamma radiation events received from a known radiation source, the gamma radiation events collected within a wide energy range relative to a collected photopeak; and
   the flood correction circuit utilizes gamma radiation events received from the known radiation source, the gamma radiation events collected within a narrow energy range relative to the collected photopeak.

7. The apparatus of claim 6, wherein the flood correction circuit utilizes gamma radiation events collected within an energy window which is 10% of the collected photopeak and which is centered about the photopeak.

8. The apparatus of claim 3, wherein the radiation detector comprises an array of semiconductor crystals selected from cadmium-zinc-telluride crystals and cadmium-telluride crystals.

9. A method of diagnostic imaging of a subject comprising:
   exposing a solid state radiation detector array to a known radiation source, the radiation detector comprising a two-dimensional array of detector elements generating a detectable signal responsive to incident gamma radiation, and each detector element comprising a distinct channel;
   detecting radiation events at each detector element;
   identifying defective and nondefective detector elements and electronically disabling defective detector elements whose response to radiation is outside of preselected specifications;
   introducing a radioactive isotope into a subject located in an imaging region;
   spinning the radiation detector array according to a preselected spin orbit;
   rotating the radiation detector array about a longitudinal axis of the subject;
   during said spinning and rotating, detecting radiation events indicative of nuclear decay to generate a plurality of planar projections of an examination region;

weighting the detected radiation events for each row of a plurality of detector elements with weighting factors to generate corrected data after the defective detector elements are disabled;

reconstructing the corrected data into an image representation of the subject in the imaging region.

10. The method of claim 9, further including:

calculating detector element correction values which normalize a spectrum of each nondefective detector element; and defining an energy window based on the energy resolution of the normalized spectra, the energy window for screening radiation events according to energy; calculating a the weighting factors for each row of a the plurality of detector elements, the weighting factor scaling each row to a nominal value when the detector is exposed to the known radiation source.

11. The method of claim 10, wherein calculating detector element correction values includes:

calculating an offset value and a gain correction factor for each detector element.

12. The method of claim 10, wherein the energy window is defined as 10% of a collected photopeak, centered about the photopeak.

13. The method of claim 9, wherein identifying defective detector elements includes:

determining whether the number of radiation events detected by each detector element exceeds a preselected threshold value;

recording as defective each detector element for which the preselected threshold value is not exceeded;

generating an energy spectrum for each detector element for which the preselected threshold value is exceeded;

analyzing the generated energy spectra for a preselected degree of energy resolution; and recording as defective each detector element which lacks the preselected degree of energy resolution.

14. The method of claim 9, wherein the array of detectors elements is a multi-channel cadmium-zinc-telluride detector array.

15. The method of claim 9, wherein the array of detectors elements further comprises:

radiation-absorbing collimator plates disposed parallel to one another for collimating the gamma radiation incident on the radiation detector array.

16. The method of claim 9, wherein spinning includes:

rotating the radiation detector array about an axis extending through a center point of the radiation detector array.

17. A method of calibrating a nuclear imaging device comprising:

exposing a solid state radiation detector to a known radiation source, the radiation detector having a two-dimensional array of detector elements generating a detectable signal responsive to incident gamma radiation, and each detector element defining a distinct channel;

detecting radiation events at each detector element;

defining an energy window based on energy resolution of normalized spectra, the energy window for screening radiation events according to energy;

identifying defective and nondefective detector elements;

calculating detector element correction values which normalize a spectrum of each nondefective detector element; and calculating a weighting factor for each of a plurality of detector element rows, after the spectra of each nondefective detector element is normalized, the weighting factor scaling each row to a nominal value when the radiation detector is exposed to a the known radiation source.

18. The method of claim 17, wherein the array of detector elements comprises a plurality of tile detector element subarrays, the method further comprising:

identifying one or more rows having a the weighting factor which is outside a preselected range of values; and rearranging the tile detector element subarrays such that the weighting factor of each of the identified one or more rows falls within said preselected range of values.

* * * * *